United States Patent

Ishigaki et al.

[11] Patent Number: 6,062,692
[45] Date of Patent: May 16, 2000

[54] VISION TESTER

[75] Inventors: Hisao Ishigaki, Toyota; Yoshikatsu Suzumura; Tetsu Tanigawa, both of Hamamatsu, all of Japan

[73] Assignee: Kowa Company Ltd., Japan

[21] Appl. No.: 09/337,614

[22] Filed: Jun. 21, 1999

[51] Int. Cl.[7] .................................................. A61B 3/02
[52] U.S. Cl. ............................................................ 351/243
[58] Field of Search ................................. 351/200, 201, 351/203, 222, 239, 243, 244, 245

[56] References Cited

U.S. PATENT DOCUMENTS 3,891,311  6/1975  Fletcher et al. ........................ 351/245
4,740,072  4/1988  Griffin et al. .......................... 351/243
5,325,136  6/1994  Salibello et al. ....................... 351/243

Primary Examiner—George Manuel
Attorney, Agent, or Firm—Adams & Wilks

[57] ABSTRACT

A vision tester comprises a slide projector for projecting a visual indication chart onto a curved display screen via a mirror rotated by a motor. The center of curvature of the curved display screen substantially coincides with the subject's eye. The rotation of the mirror causes an image of the visual indicator to be moved across the screen in a specific direction. When the subject provides a response to the moving image, the speed of image movement at the time of the response is detected and stored in a memory. The average of a plurality of such measurements is used to determine the subject's dynamic visual acuity.

6 Claims, 4 Drawing Sheets

VISION TESTER

BACKGROUND OF THE INVENTION

1. Field of the Invention

The present invention relates to a vision tester, and more particularly to a vision tester that is capable of measuring a dynamic visual acuity.

2. Description of the Prior Art

A static vision tester measures the ability to see things that are not moving, which is to say, static visual acuity. However, when a person is driving a car, it is necessary for the driver to be able to judge, quickly and accurately, obstacles, signals, signs, and so forth, and as such, emphasis is being placed on the measurement of a dynamic visual acuity. The dynamic visual acuity is the term used to designate the ability of an observer to discriminate an object when there is relative movement between the observer and the object.

The reduction of the dynamic visual acuity is accelerated and expanded by such factors as speed, fatigue and advancing age, and at high speed the dynamic visual acuity can be halved. Thus, imprecise judgement with respect to the danger involved means that driving at high speed becomes dangerous, so it is important to measure the dynamic visual acuity.

Up until now, however, there has not been any vision tester that can quantitatively measure the dynamic visual acuity, simply and accurately.

An object of the present invention is to provide a vision tester that has a simple arrangement and is able to accurately measure a dynamic visual acuity.

SUMMARY OF THE INVENTION

In accordance with the present invention, the above object is attained by a vision tester comprising means for displaying a plurality of visual indicators or a special visual indicator on a curved display screen whose center of curvature substantially coincides with the visual axis of a subject to be tested, means for moving an image of a displayed visual indicator in a predetermined direction on the curved display screen, means for detecting a speed of movement of a visual indicator image on the curved display screen when the subject responds to the moving visual indicator image, and means for determining a subject's dynamic visual acuity based on the detected moving speed.

With the above arrangement, when the subject provides a response with respect to a moving visual indicator image, the moving speed of the visual indicator image on the curved display screen is detected and the detected moving speed is used as a basis for measuring the dynamic visual acuity of the subject, thereby making it possible to provide a simple arrangement for reliably measuring the dynamic visual acuity.

Further features of the invention, its nature and various advantages will become more apparent from the accompanying drawings and following detailed description of the invention.

DESCRIPTION OF THE PREFERRED EMBODIMENT

Figure 1:
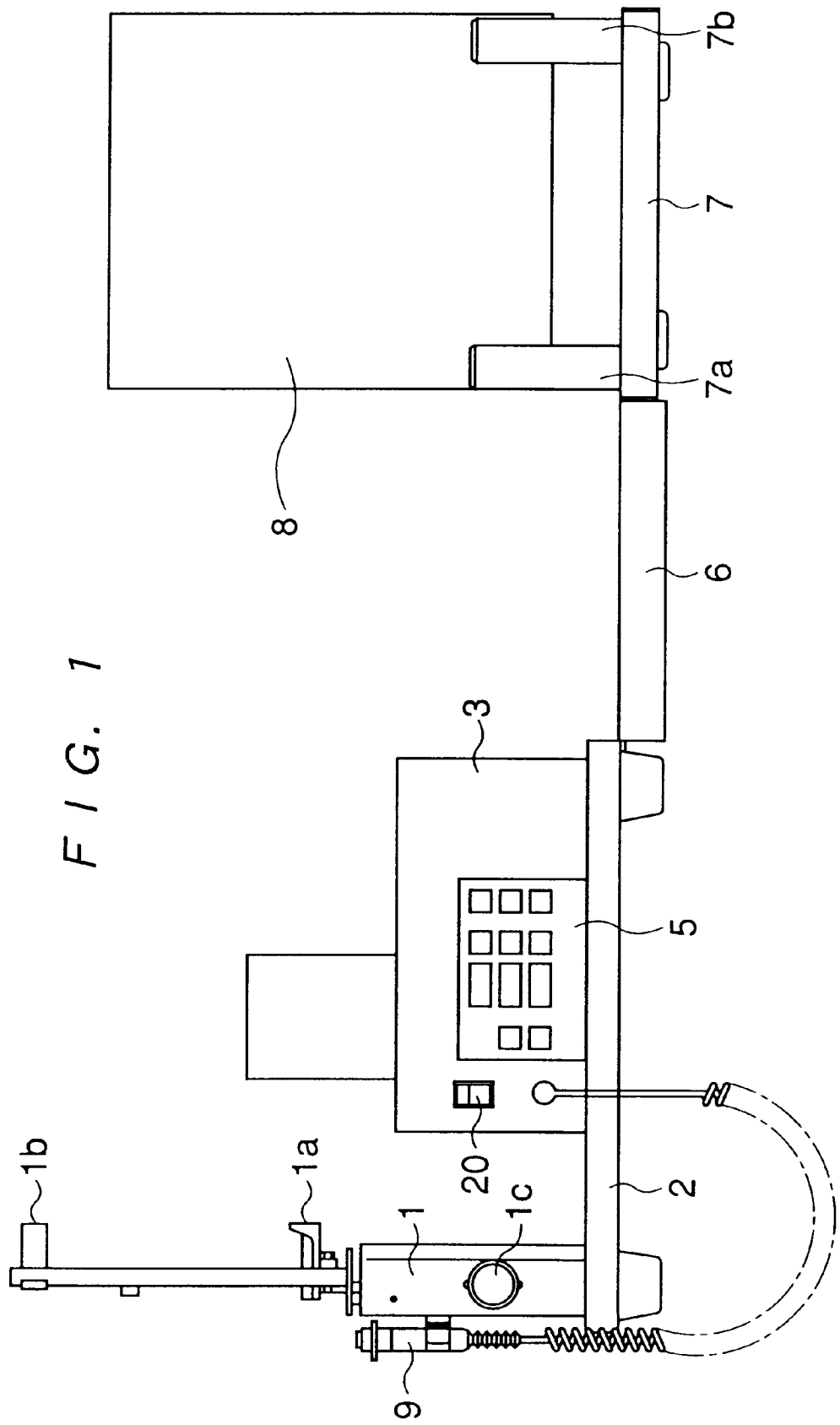
FIG. 1 is a side view showing a vision tester according to an embodiment of the present invention.
Figure 2:
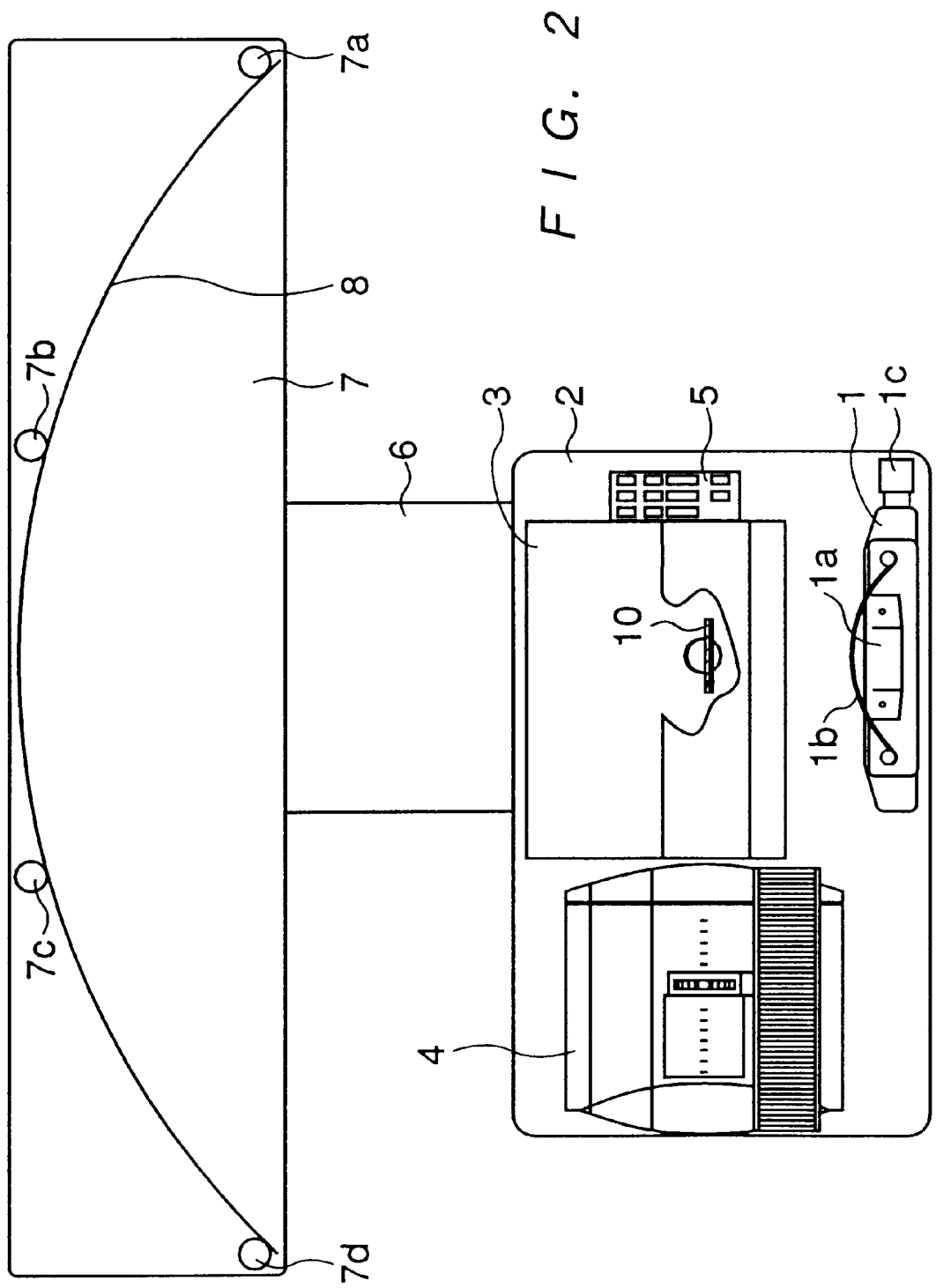
FIG. 2 is a plan view showing the vision tester according to an embodiment of the present invention.

FIGS. 1 and 2 show the arrangement of a vision tester according to an embodiment of the invention. Reference numeral 1 denotes a subject base at which the subject sits with chin against a chin-rest 1a and forehead against a headrest 1b. The height of the headrest 1b can be adjusted by means of an adjusting knob 1c. The subject base 1 is set on a base 2, which also has a control box 3 with a control panel 5, and a slide projector 4.

The base 2 is associated with a display base 7 by means of a connecting section 6. A curved display screen 8 is supported on the display base 7 by uprights 7a to 7d. A response switch 9 (not shown in FIG. 2) is attached to the subject base 1, and a power switch 20 is provided adjacent to the control panel 5.

Figure 3:
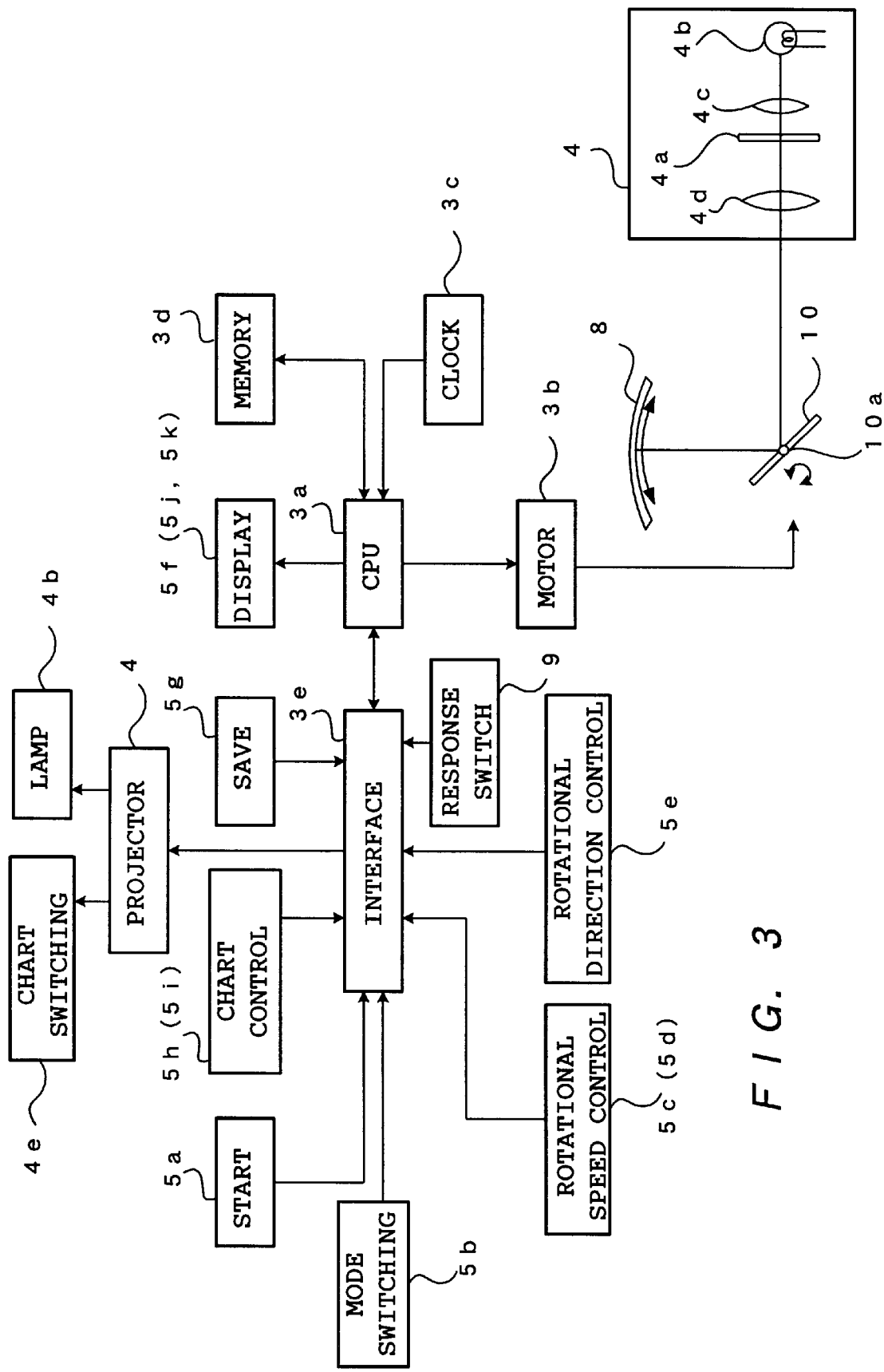
FIG. 3 is a diagram showing the arrangement of the optical and control systems of the vision tester according to an embodiment of the invention.

As shown in FIG. 3, the slide projector 4 projects an eye-chart 4a on which are printed Landolt rings spaced apart in a prescribed direction. The chart 4a, illuminated by light from a light source 4b passing through a lens 4c, is projected onto the display screen 8 via lens 4d and a mirror 10.

Under the control of a CPU 3a in the control box 3, the mirror 10 is rotated about an axis 10a by a motor 3a. The center of curvature of the curved display screen 8 substantially coincides with the position of the subject's eye or the center of rotation 10a of the mirror 10, so that, when the mirror 10 is rotated, the Landolt rings projected onto the display screen 8 move horizontally on the display screen. The speed of such movement can be adjusted by using the speed of the motor 3b to adjust the speed of rotation of the mirror 10.

The CPU 3a is operated in accordance with clocks from a clock 3c to execute a program stored in memory 3d to effect a set sequence of vision tester operations. Signals are input to the CPU 3a via an interface 3e. The CPU 3a processes the signals, stores the data in the memory 3d and outputs signals to peripheral equipments.

Figure 4:
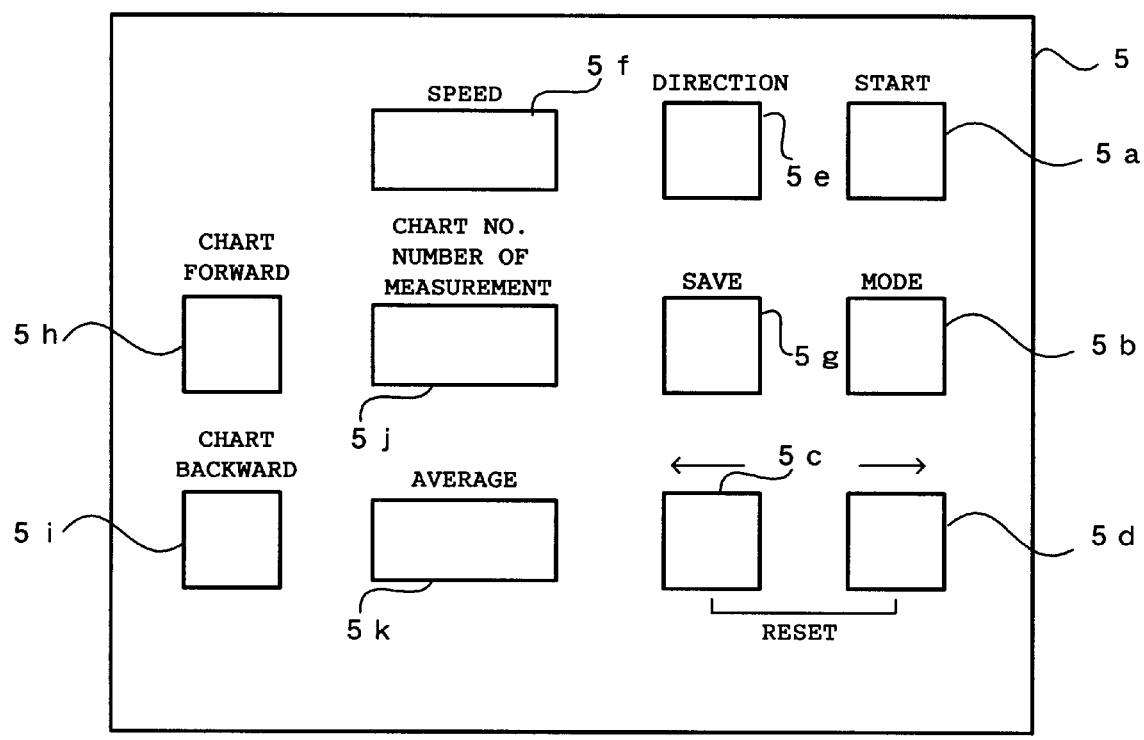
FIG. 4 is a front view showing the control panel of the vision tester according to an embodiment of the invention.

Buttons on the control panel 5, shown in FIG. 4, are used to input signals to the CPU 3a via the interface 3e. The start button 5a is used to send a signal to the CPU 3a, via the interface 3e, to start measurement of the dynamic visual acuity. This causes lamp 4b to light, and the Landolt rings eye-chart to be projected onto the display screen 8.

Mode button 5b is used to switch between automatic and manual measuring modes. Rotational speed control buttons 5c and 5d are used to control the rotational speed of the mirror 10 (and motor 3b). The initial setting is 49.5 rpm, which can be decreased or increased by using button 5c (5d). The direction of rotation of the motor can be controlled by rotational direction control button 5e. Display 5f displays the current speed of the motor 3b and of the mirror 10 driven by the motor. Save button 5g is used to store the rotational speed at the conclusion of measurement in the memory 3d.

In conjunction with a chart switching mechanism 4e, chart control buttons 5h and 5i are used to feed the chart forward and backward, respectively. This allows a charts 4a having Landolt rings of different sizes to be inserted into the light path of the projector 4. The switched chart number can be displayed by display 5j, which is also used to display how many measurements are carried out until now. Display 5k is used to display the average speed of rotation at which the subject can distinguish the direction of the spaces between the Landolt rings.

The operation of the vision tester thus arranged will now be described. First, the power switch 20 is used to switch on the electrical power, starting the motor 3b and thereby starting the mirror 10 rotating. When required, the rotational direction control button 5e can be used to change the direction of mirror rotation. Automatic or manual measurement mode is then selected by means of the mode button 5b.

In automatic mode the mirror is set to rotate at 49.5 rpm. This speed can be changed by using the rotational speed control button 5c or 5d. The operation of button 5c or 5d makes it possible to decrease or increase the rotational speed of the mirror, which can be displayed on display 5f.

Next, pressing the start button 5a causes the lamp 4b of the slide projector 4 to light, projecting the chart 4a of Landolt rings on the display screen 8. Measurement is initiated by the subject pressing the response switch 9, which causes the image of the Landolt rings to move across the screen at a high speed corresponding to the rotational speed of the mirror.

The mirror speed is reduced from the initial speed as the subject watches the movement of the chart images, until the subject can distinguish the direction of the spaces between the Landolt rings, at which point the subject presses the response switch 9. The rotational speed at which the subject presses the response switch 9 is displayed on display 5f, and can be stored in the memory 3d by pressing the save button 5g.

Pressing buttons 5c and 5d simultaneously resets the vision tester to the state before measurement was started. The next measurement operation can then be started by pressing the start button 5a. The second and subsequent measurements proceed the same way until the subject signals that he can distinguish the spaces between the moving Landolt rings, at which point the rotational speed is displayed on display 5f and stored in the memory 3d by pressing the save button 5g. The CPU uses the number of measurements and the rotational speeds to calculate an average value, which is displayed by display 5k. A value corresponding to this average is taken as the subject's dynamic visual acuity.

In automatic mode adjustment of the mirror speed and changing of the size of the Landolt rings are effected automatically by a set procedure. In manual mode, if the mirror speed has to be adjusted, it is done by using button 5c or 5d, and if Landolt rings of a different size are required, the chart control buttons 5h and 5i are used to change the chart to the one desired. Other than this, the operation proceeds in the same way as in automatic mode, with multiple measurements being taken and the average rotational speeds being displayed on the display 5k, thus completing the measurement of the subject's dynamic visual acuity.

As described in the foregoing, in accordance with this invention, an image of a visual index is moved in a predetermined direction across a curved display screen. When the subject gives a response to the moving images, the speed at which the image was moving at the time the subject gave a response is detected and used as a basis to calculate the subject's dynamic visual acuity. Thus, the invention makes it possible to reliably measure the dynamic visual acuity with a simplified arrangement.

What is claimed is:

1. A vision tester comprising:

means for displaying a plurality of visual indicators or a special visual indicator on a curved display screen whose center of curvature substantially coincides with the visual axis of a subject to be tested, means for moving an image of a displayed visual indicator in a predetermined direction on the curved display screen, means for detecting a speed of movement of a visual indicator image on the curved display screen when the subject responds to the moving visual indicator image, and means for determining a subject's dynamic visual acuity based on the detected moving speed.

2. A vision tester according to claim 1, wherein the image of a displayed visual indicator is moved across the curved display screen by a rotating mirror.

3. A vision tester according to claim 1, wherein a speed of movement of a visual indicator image on the curved display screen can be adjusted.

4. A vision tester according to claim 1, wherein the visual indicators can be selected.

5. A vision tester according to claim 1, wherein the visual indicator is Landolt rings and the subject responds in terms of the direction of spaces between the Landolt rings.

6. A vision tester according to claim 1, wherein the dynamic visual acuity is measured a plurality of times and the outcome is statistically processed.

* * * * *